United States Patent [19]

Nickel

[11] Patent Number: 4,788,987

[45] Date of Patent: Dec. 6, 1988

[54] APPARATUS FOR MEASURING THE LOCATIONAL AND ATTITUDINAL CHANGE OF A RIGID BODY IN SPACE

[75] Inventor: Bernd Nickel, Lorsch, Fed. Rep. of Germany

[73] Assignee: Siemens Aktiengesellschaft, Berlin and Munich, Fed. Rep. of Germany

[21] Appl. No.: 18,427

[22] Filed: Feb. 25, 1987

[30] Foreign Application Priority Data

Feb. 27, 1986 [DE] Fed. Rep. of Germany ....... 3606446

[51] Int. Cl.⁴ ............................. A61B 5/05; A61B 5/10
[52] U.S. Cl. ...................................... 128/777; 433/69; 324/207
[58] Field of Search ............... 128/774, 777, 781, 782; 433/68, 69; 33/513, 514; 324/207

[56] References Cited

U.S. PATENT DOCUMENTS

| | | |
|---|---|---|
| 3,390,459 | 7/1968 | Seidenberg . |
| 3,526,886 | 9/1970 | Lubich ................. 324/207 |
| 4,303,077 | 12/1981 | Lewin et al. . |
| 4,330,276 | 5/1982 | Becker et al. .......... 433/69 |
| 4,354,836 | 10/1982 | Santoni . |
| 4,371,836 | 2/1983 | Nickel et al. . |
| 4,447,207 | 5/1984 | Kataoka et al. . |
| 4,688,037 | 8/1987 | Krieg ................. 324/207 |

Primary Examiner—Kyle L. Howell
Assistant Examiner—John C. Hanley
Attorney, Agent, or Firm—Hill, Van Santen, Steadman & Simpson

[57] ABSTRACT

An apparatus for measuring the location and attitude, as well as, locational and attitudinal changes of a rigid body in space has a transmission system which is composed of at least three current-permeated elements arranged at right angles relative to one another and supplied with different operating frequencies by an alternating current generator. The alternating magnetic field thereby generated are received by a plurality of magnetic field sensors arranged perpendicular to one another. The magnetic field sensors are attached to the rigid body. An evaluation electronic instrument separately evaluates the signals obtained from the three different alternative fields and converts them into quantities corresponding to the position to at least one point of the body. The magnetic field sensors are preferably magnetic coils which are arranged perpendicular to one another on a coil body of non-ferromagnetic material.

12 Claims, 4 Drawing Sheets

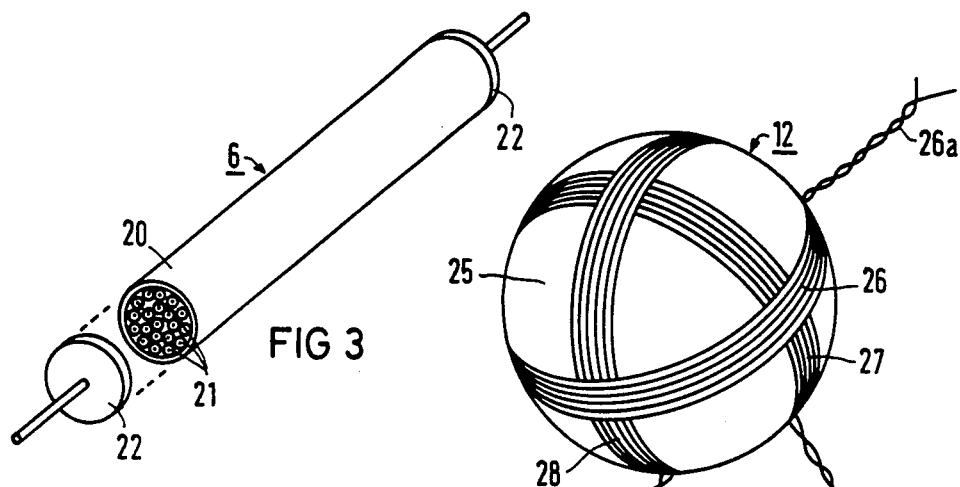
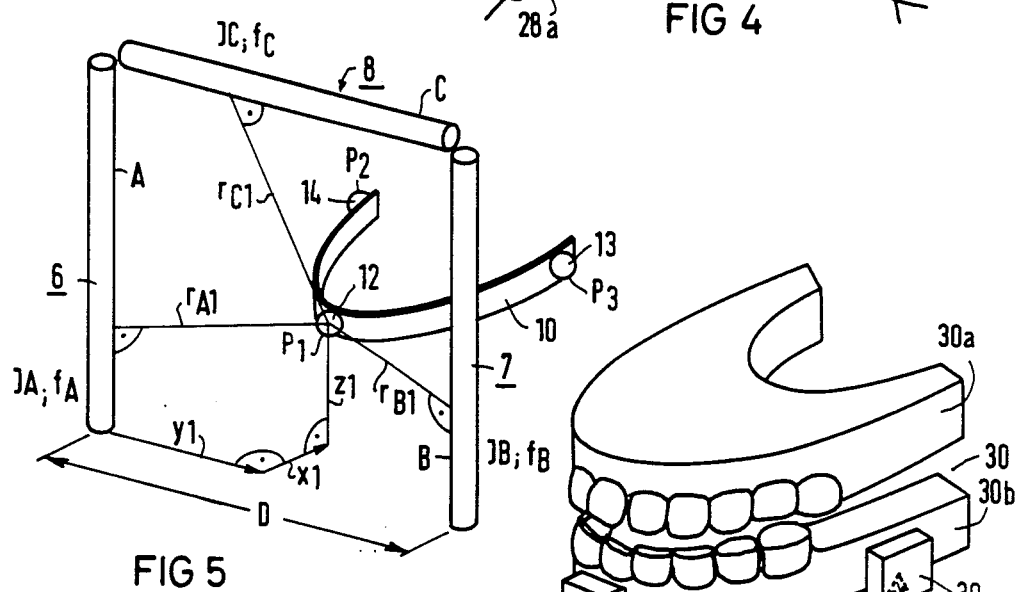
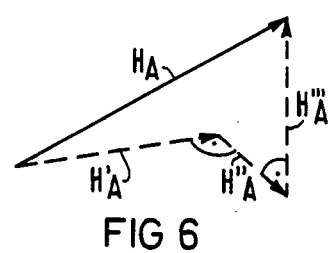
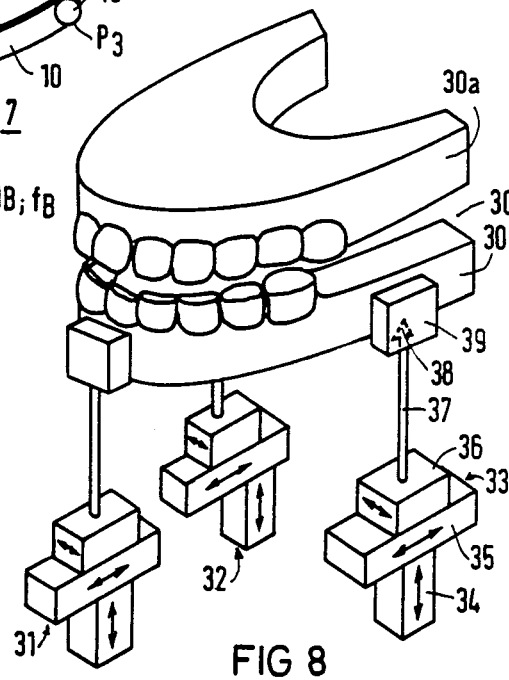

4,788,987

APPARATUS FOR MEASURING THE LOCATIONAL AND ATTITUDINAL CHANGE OF A RIGID BODY IN SPACE

BACKGROUND OF THE INVENTION

1. Field of the Invention

This invention relates generally to an apparatus for determining the location and attitude of a rigid body in space and, in particular, to a device for measuring movement of a lower jaw of a patient.

2. Prior Art

A typical prior art device for measuring the location and attitude, as well as, the locational and attitudinal changes of a rigid body in space is disclosed by German Patent Application P 28 52 764. The disclosed device is preferably utilized in gnathology and especially serves for measuring movement of the lower jaw of a patient. In this device a field generator in the form of a crossed permanent magnet is located on the lower jaw of a patient. The magnet generates a defined irregular magnetic field. A plurality of magnetic flux sensors are used to measure the flux of the magnetic field, as well as, changes in the field flux. The magnetic flux sensors are provided at a stationary location relative to the lower jaw of the patient and ar located at a known distance from the field generator. In this device, the magnetic flux sensors have the form of rod-shaped antennas which are arranged in pairs in three mutually perpendicular planes. The changes in field flux registered by the magnetic flux sensors are converted into electrical signals which are appropriately processed in a signal evaluation instrument. These electrical signals supply information corresponding to the location and/or locational change of the lower jaw. In the disclosed device, it is assumed that corresponding rotational signals, angles $\alpha$, $\beta$, $\gamma$, can be acquired upon interpretation of the asymmetrical field generated by the field generator in addition to acquiring the translational motion in the three planes x, y, z.

Particularly in gnathology, it has been shown that the field generator, which is secured to the lower jaw of the patient, cannot exceed certain dimensions if the chewing function is not to be influenced during a measuring process. A further requirement is that access to the test subject, that is to the patient's mouth, must be assured without interfering the freedom of mobility of the lower jaw being negatively influenced by the arrangement of the magnetic flux sensors. In order to assure the latter condition, the magnetic flux sensors must be located a significant distance from the field generator. Such an arrangement, however, results in extremely small useful signals derived from the rotational motion of the lower jaw. These signals are frequently masked by disturbances of an electrical and magnetic nature, for example, due to noise of the evaluation electronics, or due to influences from disturbing fields of the environment, etc. In comparison to the signals that are obtained from the translational motion of a selected measuring point the rotational motion signals do not yield the desired precision in the identification of other point motions, for example, of the condyle paths during chewing motions.

German OS 33 12 245 discloses an apparatus for the diagnosis of lower jaw movements wherein the movement of the lower jaw is determined by three measuring points. To accomplish this a band is attached to the head of the patient. This band has affixed to it position detectors at three different points in a predetermined relative attitude with respect to the upper jaw. Spot or point light sources, which are carried by a shackle, are held in a predetermined mutual relative attitude and are orientated with position detectors. Point light sources correspond to the measuring points, that is, they define a plane representing the lower jaw. The shackle is fixed via a coupling piece with respect to the lower jaw of the patient. The point light sources are connected via light guides to a main light source.

The motion of the lower jaw can thus be determined with the apparatus with the assistance of optical auxiliary equipment. For the purpose of reproduction of the lower jaw motion, a total motion of the lower jaw is converted into the motion of three reproducible reference points which correspond to the individual measuring points. The motion resulting therefrom can be correspondingly reproduced using a lower jaw model.

A distinct disadvantage of this prior art device is that the information generators, that is the light sources, must be arranged outside of the oral cavity and, thus, outside of the patient's head. The use of light or even sound is undesirable since it cannot penetrate tissue without introducing error into the measurement.

The prior art mechanical method disclosed by German OS 30 02 267 similarly operates with three measuring points. The disclosed method also has the disadvantage that the natural chewing function is negatively influenced by the weight of the apparatus which exerts a force on the jaw of the patient. As a result the information acquired may be erroneous.

The present invention overcomes these drawbacks in the prior art.

SUMMARY OF THE INVENTION

An objective of the present invention is to provide an apparatus with which a complete and exact measurement can be made of the motion of a rigid body in space, particularly a lower jaw of a patient.

With the use of Hall generators, the reception system portion of the present invention can be composed of an antenna system which is constructed in a fashion similar to that in the cited German patent application P 28 52 764. Advantageously, however, the reception system is composed of magnetic field sensors in the form of magnetic coils arranged perpendicular relative to one another and which pick up alternating fields in accord with three operating frequencies. The three operating frequencies are generated by a transmission system of the present invention.

As a result of employing magnetic coils as reception elements, the possibility is thus opened up that the transmission system can be arranged either at the test subject or on a structure which is stationary in comparison to the test subject.

Although there is no constraint in the selection of the arrangement of the reception system and transmission system, it is nonetheless advantageous, particularly in the field of gnathology, to allocate the passive portion, that is the reception system, not on the stationary structure (patient's head) but on the movable part (lower jaw). Given this arrangement the transmission power can be greatly increased, thereby more effectively suppressing external disturbing influences. Further, this arrangement also provides greater latitude in the design of the alternating field generator. This is especially significant in order to be able to optimally adapt the attitude of the field generators with respect to the linearity of the acquired signals of the reception and transmission system.

In the present invention the transmitter is composed of three current-permeated conductors extending essentially over the jaw width or, respectively, over the patient's mouth. The current-permeated conductors can be composed of one or more individual conductors. Although the conductors can be arbitrarily arranged on the lower jaw it is advantageous to arrange them in one plane and also to arrange them perpendicular and, parallel to one another with respect to their longitudinal axes so as to form a U-shaped configuration. The conductors be part of a head frame or an eyeglass frame which fits about the patient's head.

The reception system is composed of three, preferably spherical, reception elements which are arranged such that they define a plane, that is they are not colinear. Each reception element contains a coil bobbin of non-ferromagnetic material on which three coils are arranged perpendicular to one another. The windings of the coils are inserted into corresponding grooves in the coil bobbin. The coil bobbin can comprise a spherical, cubical or other suitable shape. The three coil bobbins are arranged on a clip-shaped carrier element corresponding to the dental arch and are arranged thereon in a predetermined fixed spacing from one another. The spacing however may be arbitrarily selected. The fastening to the lower jaw can be made by means of suitable adhesions.

The signals received by the reception elements are supplied to an evaluation electronic instrument which derives information regarding the movement of the three measuring points from the strengths of the magnetic fields at the measuring points based on the following general relationship $$H = \frac{n \cdot I}{2 \cdot \pi \cdot r}$$

whereby n=the number of current-permeated conductors; I=current intensity and r =direct spacing between the transmitter and receiver. The evaluation electronic instrument can be designed with discrete component parts or a commercially available electronic computer which is suitable for the present purpose could be utilized.

It is advantageous to place one of the measuring points in the middle between the two front incisors of a row of teeth (incisal point) because the greatest translational movement is to be anticipated at this point. Although specific functional information regarding the chewing function of a patient can be obtained from a single measuring point, additional information can be obtained using two other measuring points from which the movement of any arbitrary point of the lower jaw can be calculated. For example, by using two other measuring points information regarding the movement of the condyle paths can be determined.

As known, for example, from the cited German OS 33 12 245, it is advantageous to move a tooth model three dimensionally in space with the acquired information. Motor drives can be attached through bearing locations to points on the tooth model which correspond to the location of the reception elements in the reception system of the present invention. These motor drives are driven in accord with the acquired measured signals obtained from the reception system.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, and the several figures of which like reference numerals identify like elements, and in which:

FIG. 3 is a perspective view of one of the transmission elements used in the transmitter system;

FIG. 4 is an enlarged perspective view of one of the reception elements used in the receiver system;

FIG. 5 is a geometrical illustration which depicts the relationship between the transmitter and receiver;

FIG. 6 is a vector diagram of the resulting magnetic field;

FIG. 8 is a perspective view of a lower jaw dentition model and FIG. 9 and FIG. 10 are cross-sectional views of the coil bobbin used in FIG 1.

DESCRIPTION OF THE PRESENTLY PREFERRED EMBODIMENTS

Figure 1:
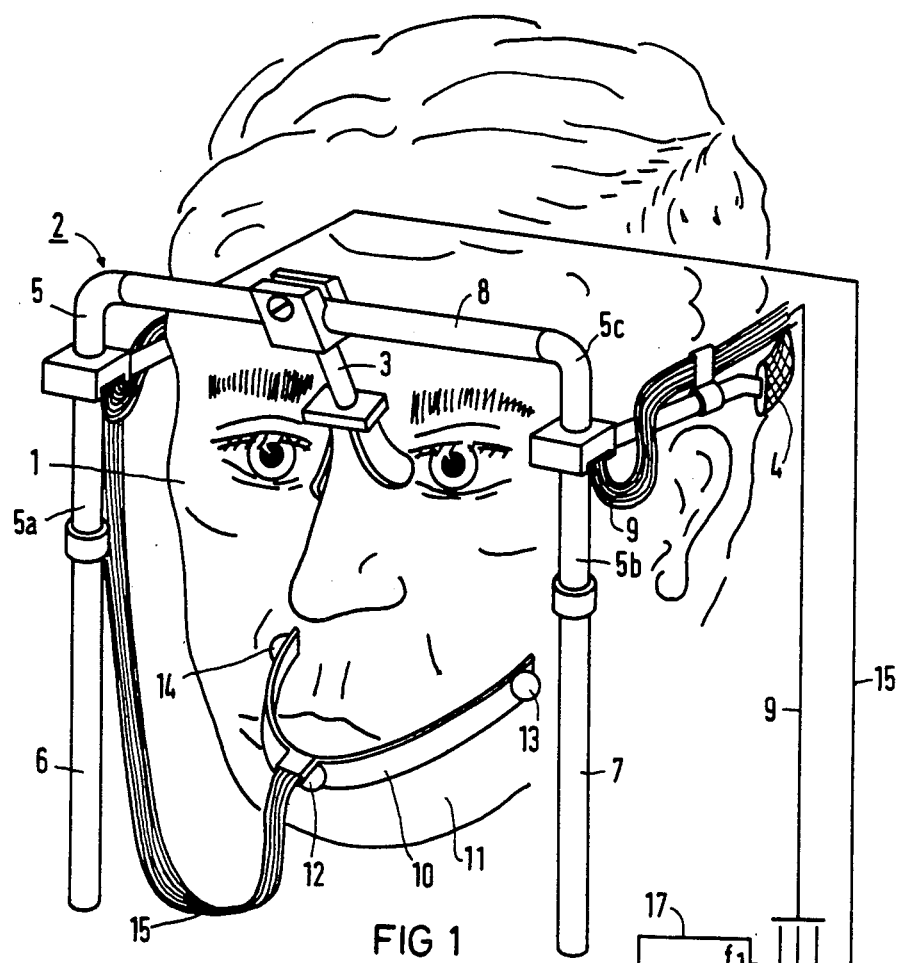
FIG. 1 is a perspective view of the apparatus of the present invention used for measuring the lower jaw movement of a patient.

The present invention has a general applicability but is preferably used in an embodiment as shown in FIG. 1. This preferred embodiment is intended for measuring the movement of the lower jaw of a patient. A head frame 2 is provided at a patient's head 1, this head frame 2 being secured to the patient's head 1 in a suitable way, for example, by means of a nose support member 3 and a belt band 4. The head frame 2 has an inverted U-shaped frame 5 whose legs 5a, 5b and 5c are arranged at right angles relative to one another that is leg 5a lies at a right angle with respect to leg 5c and leg 5b lies at a right angle with respect to leg 5c, and lie in one plane, as shown in FIG. 1. The tube frame 5 contains rod-shaped transmission elements 6, 7 and 8 which, corresponding to the arrangement of the legs 5a, 5b and 5c, are likewise respectively arranged perpendicular to one another (5a to 5c, 5b to 5c) and parallel to one another (5a to 5b) with respect to their longitudinal axes and which also lie in one plane. Electrical energy is supplied by a multi-lead cable 9 which is contained within the tube frame 5.

A clip-shaped retaining part 10 is adapted to and secured to the lower jaw 11 of the patient. The retaining part 10 may be secured to the lower jaw 11 by suitable adhesive, for example, by means of impression compound. Three reception elements 12, 13 and 14 are secured to the clip-shaped retaining part 10 such that they have a fixed, defined spacing from one another. The arrangement is arbitrary but in the preferred embodiment the three reception elements form the corner points of a triangle, preferably an equilateral triangle. With this arrangement the front reception element 12 is located centrally between the two front incisors. A relatively large signal can thus be generated with respect to the translational movement of the jaw 11. The signal lines leading from the three reception elements 12, 13 and 14 are combined in a signal ribbon cable 15. The signal cable 15 leads to an evaluation electronics instrument 16. The cable 9 is connected to an alternating current generator 17 which generates alternating current having three different operating frequencies $f_1$, $f_2$ and $f_3$. The three operating frequencies lie in a range greater than 10 kHz. In FIG. 1 the signal cable 15 and the supply cable 9 are shown in part only as a single line for the sake of clarity, in practice, a plurality of lines lead from every reception element to the evaluation electronic instrument.

Figure 2:
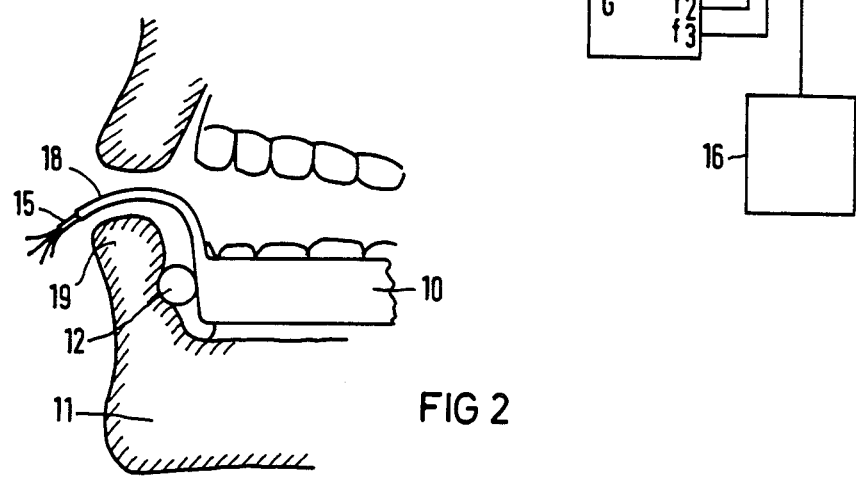
FIG. 2 is a cross-sectional detailed view of the mouth portion of the patient shown in FIG. 1.

In order to prevent the cable 15 from lying on the lower lip of the patient, which may prevent the patient from carrying out a natural chewing motion under any given condition, the cable 15 is guided in a rigid guide tube 18 which is secured to the retaining part 10. The guide tube 18, as can be seen in FIG. 2, is bent such that it lifts the cable 15 above the lower lip 19 of the patient.

The structure of the transmission elements is shown in FIG. 3, specifically shown is transmission element 6. The transmission element 6 contains an outer enveloping tube 20 which can either be part of the tubular frame 5 or can be a separate tube secured to leg 5a of the frame 5. A plurality (preferably 20) of individual electrical conductors 21 are arranged parallel to one another in the tube 20 with each of the ends of the conductors 21 being electrically connected to one another by suitable connecting elements 22. The individual conductors 21 are powered from an alternating current generator 17, as shall be set forth later, and generate an electrical alternating field with a given current flux. The conductor or tube length is arbitrary, however, it must be far greater than the effective diameter of the transmission element, that is the diameter of all of the conductors contained in the tube 20. In the present example, it is advantageous to dimension the length of the transmission elements 6, 7 and 8 such that they cover the aperture of the mouth or the jaw width.

The design of the reception elements 12, 13 and 14 shall be described with reference to FIG. 4 which illustrates the reception element 12. Each reception element is composed of a coil bobbin 25 (about 4 mm in diameter) of non-ferromagnetic material and is also composed of coils 26, 27 and 28 which are offset by 90° relative to one another. Terminal leads 26a, 27a, 28a are first separately conducted to exit from the patient's mouth and then are conducted to the evaluation electronic instruments 16 as a common signal cable 15. The terminal leads 26a, 27a and 28a may be attached to the clip-shaped retaining part 10 by any suitable manner.

Figure 9:
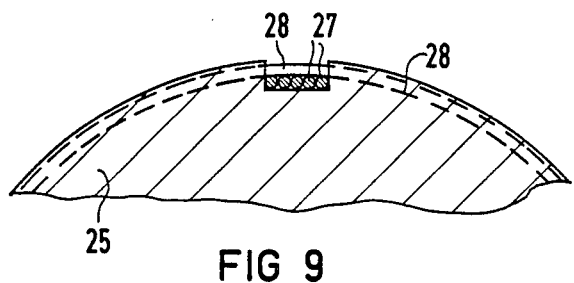
Figure 10:
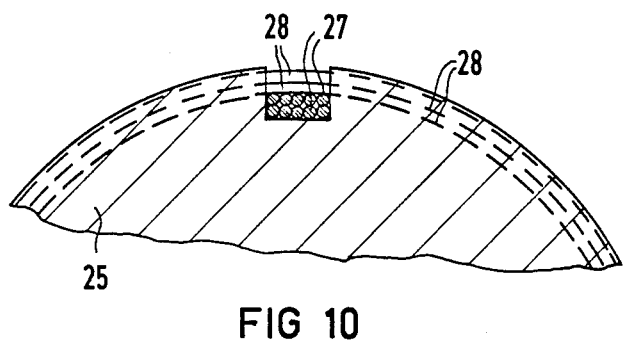

For retaining the windings of the coils 26, 27 and 28, the coil bobbin 25 has grooves corresponding to the coil width into which the windings are laid in either a one-ply or multi-ply configuration. As shown, in FIGS. 9 and 10 the coil bobbin 25 may be spherical, although other shapes are also conceivable as long as the corresponding grooves for the coil windings are present.

Figure 7:
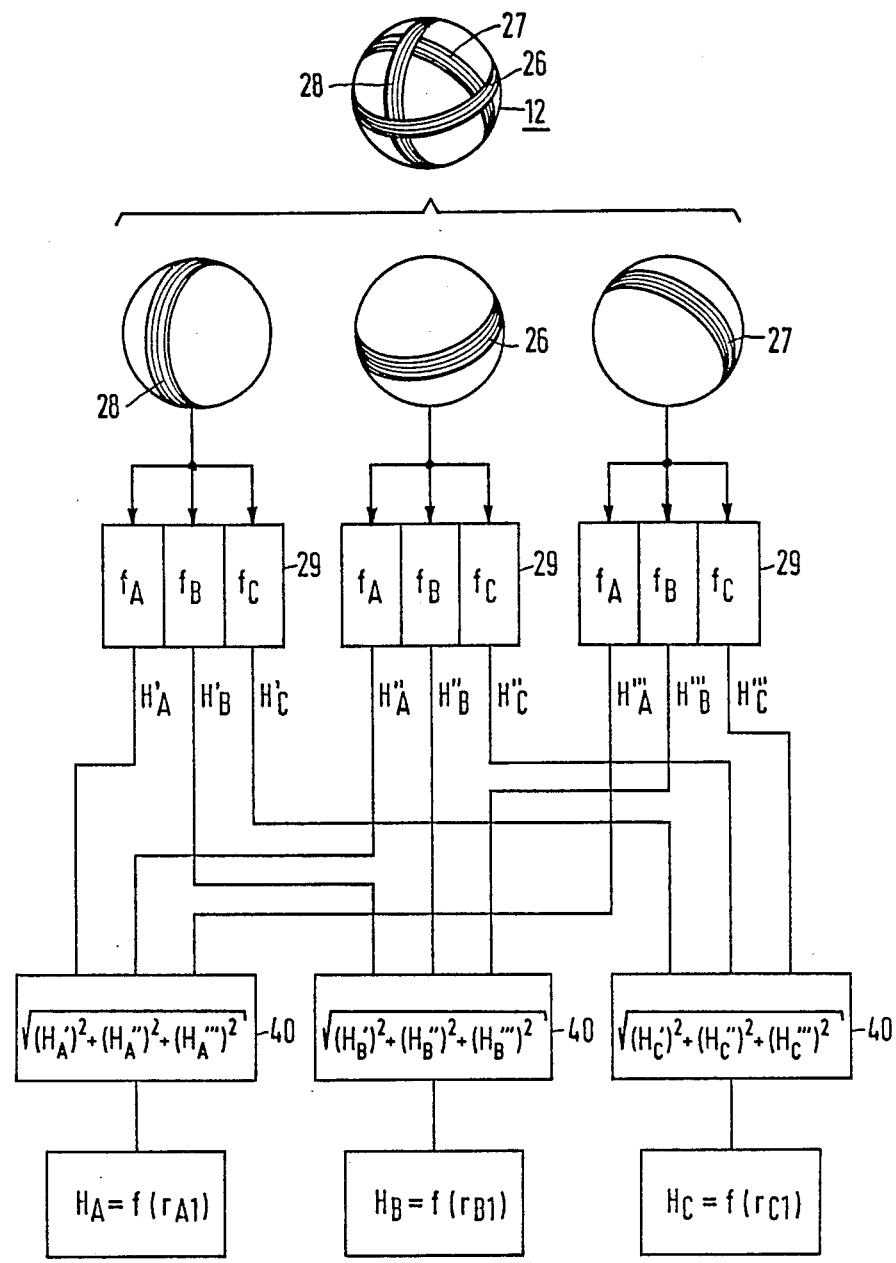
FIG. 7 is a schematic illustration of a fundamental circuit arrangement for the evaluation of signals received from a reception element.

The measurement and evaluation principles shall be explained in reference to FIGS. 5, 6 and 7. For the sake of greater clarity, the currents (I), frequencies (f) and field (H) allocated to the transmission elements 6, 7 and 8 are identified with the letters A for the transmission element 6, B for the transmission element 7 and C for the transmission element 8.

The alternating current generator 17 supplies the three transmission elements 6, 7 and 8 with respectively different operating frequencies $f_A$, $f_B$, and $f_C$. These operating frequencies are in a range above 10 kHz. The transmission elements 6, 7 and 8 in the form of conductors 21 contained therein are permeated by currents $I_A$, $I_B$ and $I_C$, respectively. Current flux generates magnetic fields $H_A$, $H_B$ and $H_C$ around the conductors and around the transmission elements. The following general relationship describes this magnetic field $$H = \frac{n \cdot I}{2 \cdot \pi \cdot r}$$

whereby n is the plurality of existing, current-permeated conductors; r is the respective, direct spacing of the current-permeated conductor (transmitter) from a measuring point P at which the alternating field is measured, that is the distance of the transmitter from a reception element.

It may be derived from the relationship given above that for a constant current I, the magnetic field H depends only on the spacing r, that is on the distance of the transmitter from the reception element, which is the measuring point.

In order to exactly measure the alternating magnetic fields emitted at measuring points (P1, P2, P3), see FIG. 5, by the transmission elements, each of the reception elements 12, 13 and 14 has three coils 26, 27 and 28 arranged at a right angle relative to one another. Reception element 12 is located at measuring point P1, reception element 13 is located at measuring point P3 and reception element 14 is located at measuring point P2.

As illustrated in FIG. 5 the three transmitters A, B, C generate magnetic fields $H_A$, $H_B$, $H_C$ having the respective spacings $r_{AI}$, $r_{BI}$ and $r_{CI}$ with reference to the reception element 12 at the measuring point P1.

For example, the transmitter A comprising the transmission element 6 generates the field $H_A$ at the measuring point P1 which has the coordinates $x_1$, $y_1$, $z_1$ in a coordinate system x, y, z. This field $H_A$ whose size and direction are defined in FIG. 6 by the vector H can be represented by the vector components Hhd A , $H_A''$, and $H_A'''$, whereby each of these components is a vector orientated perpendicular to the other two vectors. From the following mathematical equation $$H_A = \sqrt{(H_A')^2 + (H_A'')^2 + (H_A''')^2} = \frac{n \cdot I}{2 \cdot \pi \cdot r_{A1}}$$

the relationship between the magnetic field ($H_A$) and the interval between the transmitter and receiver ($r_A$) for the corresponding measuring point (P1) can be determined. It can be appreciated that the measurement of the magnetic field $H_A$ is not dependent on the attitude of the reception element (12) at the measuring point (P1).

The same analysis as set forth above can be performed for the identification of $r_{BI}$ and $r_{CI}$. As depicted in the diagram of FIG. 7 signals which are picked up by the individual coils 26, 27 and 28 of the reception element are first separated from one another in frequency filters 29 which separate signal frequencies $f_A$, $f_B$ and $f_C$ and are then processed in operational computers 40 as set forth above, whereby the field strength (H) as a function of the distance (r) of the transmitter from the measuring location is obtained as a result of the computational operation. Upon application of known coordinate transformations, the vales for $r_A$, $r_B$ and $r_C$ can be converted into any arbitrary coordinate system, for example into a Cartesian coordinate system which has the coordinates x, y, z in accord with the illustration in FIG. 5.

With the three reception elements 12, 13 and 14 on the lower jaw, nine information signals are acquired regarding the movement of the measuring points P1, P2 and P3. Since the three measuring points P1, P2 and P3 are geometrically defined by location of the reception elements 12, 13 and 14 on the reception clip 10, the movement of the lower jaw can be completely described by the obtained signals x, y, z for the three measuring points. The evaluation electronic instrument 16 which evaluates the information about the movement of the three measuring points from the strength and direction of the magnetic fields can be fashioned with discrete components, however, a suitable commercial available electronic computer can also be employed for this purpose. Although it is possible to obtain specific functional statements about the chewing function of a patient with a single measuring point, the incorporation of two other measuring points has the additional advantage that the movement of an arbitrary point at the lower jaw can be identified, in particular the movement of the condyle paths.

Furthermore, information derived from the three measuring points may be utilized to move a dentition model in three-dimensional space. Such an arrangement is shown in the schematic illustration in FIG. 8.

A dentition model 30 is composed of a stationary upper jaw part 30a and a lower jaw part 30b which is arranged to be movable with respect to the upper jaw part 30a. The lower jaw part 30b is seated in three-dimensionally mobile fashion and contains movement transmitters 31, 32 and 33 connected to points which correspond to the locations of the three reception elements 12, 13 and 14 in the reception system shown in FIG. 1. Each of these motion transmitters respectively contain three drivers 34, 35 and 36 acting in planes perpendicular to one another and also contain a transmission pin 37 which is connected by a toe bearing 38 to a transmission element 39 which in turn is rigidly connected to the lower jaw part 30b. The three drives 34, 35 and 36 receive information regarding one point, which corresponds to a measured point on a patient's jaw, for example, point P2 and are displaced in the three planes in accord with the received information. This displacement motion is forwarded to the lower jaw model by the transmission pin 37 and the toe bearing 38. The analogous case applies to the other two motion transmitters 31 and 32. The motion of the dentition model can be exactly duplicated with the measured values obtained from the arrangement set forth above.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative not in a limiting sense.

I claim:

1. An apparatus for measuring the location and attitude, as well as, locational and attitudinal changes of a jaw of a patient, comprising:
   transmission system means for generating three different magnetic fields comprising three current-permeated elements arranged relative to one another in a U-shaped configuration in one plane and supplied respectively with three different respective operating frequencies by an alternating current generator, each of said current-permeated elements having at least one conductor which is surrounded by an enveloping tube which is attached to means for securing the current-permeated elements in a predetermined fixed position with respect to a patient's head;
   reception system means having three reception elements for receiving said magnetic fields generated by the transmission system means, said reception elements being arranged in one plane on a retaining part shaped to correspond to a dental arch at a predetermined, fixed spacing from one another, said reception elements including coils capable of generating signals in response to the three different operating frequencies; and
   evaluation electronics means connected to said reception elements for receiving said signals from each coil representative of said three different alternating fields and for separating the signals into individual components;
   wherein said evaluation electronics means further includes means for converting said components into signal quantities corresponding to the position of at least one reception element with respect to the location of the current-permeated elements.

2. The apparatus described in claim 1 wherein said reception elements coils are arranged on a coil bobbin of spherical shape and of non-ferromagnetic material said coils being orientated perpendicular to one another on said bobbin, and wherein said coil bobbin has grooves corresponding to the coil width of said magnetic coils, windings of said magnetic coils being inserted into said grooves single-ply or multi-ply.

3. The apparatus described in claim 2, wherein said reception system means further comprises signal lines connected to said magnetic coils, said signal lines being contained in a guidance part means to prevent said signal lines from contacting a lower lip of the patient.

4. The apparatus described in claim 1, wherein the arrangement of said reception elements forms the corner points of an equilateral triangle.

5. The apparatus described in claim 4, wherein one of said reception elements is positioned at a location on said retaining part corresponding to an incisal point of the dental arch.

6. The apparatus described in claim 1 wherein said current-permeated elements are conductors each of which is a length sufficient to span the width of the jaw of a patient's mouth.

7. The apparatus described in claim 1, wherein said evaluation electronics means has frequency filter means to separate the reception element signals into said separate individual components, said signal quantities corresponding to the position of at least one reception element being obtained therefrom.

8. The apparatus described in claim 7 wherein said apparatus further comprises displacement drive means for controlling lower jaw simulation of a dentition model, said drive means being connected to be driven with said signal quantities corresponding to the positions of the at least one reception element.

9. An apparatus for measuring the location and attitude, as well as, locational and attitudinal changes of a jaw of a patient, comprising:
   transmission system means for generating three different alternating magnetic fields comprising three current-permeated elements arranged in a U- shaped configuration in one plane and supplied respectively with three different respective operating frequencies by an alternating current generator, each of said current-permeated elements comprising a plurality of individual conductors surrounded by an enveloping tube the ends of said conductors being electrically connected to one another, each enveloping tube being attached to means for securing the current-permeated elements in a predetermined fixed position in relation to a patient's head, said current-permeated conductors each having a length which roughly corresponds to the width of the jaw of the patient;

reception system having three reception elements arranged on a retaining part corresponding to a dental arch attachable to the jaw of a patient, said three reception elements arranged at a predetermined, fixed spacing from one another for measurement of lower jaw movement of said patient, said reception elements lying in one plane and their arrangement forming the corners of a equilateral triangle, thereby defining three predetermined measuring points, each of said three reception elements having at least three magnetic field sensors for receiving said magnetic fields generated by said transmission system, said magnetic field sensors being coils which are arranged on a coil bobbin of non-ferromagnetic material perpendicular to one another; and evaluation electronic means connected to said reception system for receiving signals from said coils which are representative of said three different alternating magnetic fields;

wherein said evaluation electronics include means for converting said signals into quantities corresponding to positions of said three measuring points with respect to said current-permeated elements.

10. The apparatus described in claim 9, wherein said coil bobbin of each of said reception elements is spherically shaped.

11. The apparatus described in claim 9 wherein said evaluation electronics means includes frequency filter means for separating the signals from said coils into individual signal components respectively representative of said three different alternating magnetic fields prior to conversion by the means for converting.

12. An apparatus for measuring the location and attitude, as well as, locational and attitudinal changes of a jaw of a patient, comprising:

transmission system means for generating three different alternating magnetic fields comprising three current-permeated elements arranged in a U-shaped configuration and respectively supplied with three different respective operating frequencies by an alternating current generator, said current-permeated elements being arranged in one plane, each element comprising a plurality of individual conductors which are surrounded by an eveloping tube connected to means for securing the current-permeated elements in a predetermined fixed position in relation to a patient's head;

reception system means having three reception elements attachable to the lower jaw of the patient at predetermined measuring points in one plane in an arrangement forming the corner points of an equilateral triangle, each of said reception elements having three magnetic field sensor means for receiving said magnetic fields generated by the transmission system, said magnetic field sensors comprising coils which are arranged on a coil bobbin of non-ferromagnetic material in an orientation perpendicular to one another; and evaluation electronics means connected to said reception elements for receiving signals from said coils representative of said three different alternating magnetic fields, said evaluation electronics means including means for separating each received signal through frequency filters, and for issuing signal quantities corresponding to the relative positions of the reception elements with respect to the respective current-permeated elements from the separated signals.

* * * * *